United States Patent
During

(10) Patent No.: US 10,736,894 B2
(45) Date of Patent: Aug. 11, 2020

(54) METHODS OF TREATING DEVELOPMENTAL SYNDROMES WITH PDE10A INHIBITORS

(71) Applicant: Ovid Therapeutics Inc., New York, NY (US)

(72) Inventor: Matthew During, Weston, CT (US)

(73) Assignee: Ovid Therapeutics Inc., New York, NY (US)

( * ) Notice: Subject to any disclaimer, the term of this patent is extended or adjusted under 35 U.S.C. 154(b) by 0 days.

(21) Appl. No.: 16/277,037

(22) Filed: Feb. 15, 2019

(65) Prior Publication Data

US 2019/0247394 A1   Aug. 15, 2019

Related U.S. Application Data

(60) Provisional application No. 62/631,077, filed on Feb. 15, 2018.

(51) Int. Cl.
*A61K 31/501* (2006.01)
*A61K 31/497* (2006.01)
*A61K 31/47* (2006.01)
*A61P 25/00* (2006.01)
*A61K 31/4709* (2006.01)

(52) U.S. Cl.
CPC ........ *A61K 31/501* (2013.01); *A61K 31/4709* (2013.01); *A61K 31/497* (2013.01); *A61P 25/00* (2018.01)

(58) Field of Classification Search
CPC ..... A61K 31/501; A61K 31/497; A61K 31/47
USPC ................ 514/252.05, 255.05, 311
See application file for complete search history.

(56) References Cited

U.S. PATENT DOCUMENTS

| | | |
|---|---|---|
| 8,354,411 B2 | 1/2013 | Taniguchi et al. |
| 8,435,995 B2 | 5/2013 | Taniguchi et al. |
| 8,513,251 B2 | 8/2013 | Taniguchi et al. |
| 8,778,944 B2 | 7/2014 | Taniguchi et al. |
| 8,916,566 B2 | 12/2014 | Taniguchi et al. |
| 8,946,230 B2 * | 2/2015 | Allen ............ C07D 401/14 514/255.05 |
| 9,090,586 B2 | 7/2015 | Yoshikawa et al. |
| 9,150,588 B2 | 10/2015 | Taniguchi et al. |
| 9,550,756 B2 | 1/2017 | Taniguchi et al. |
| 9,610,261 B2 | 4/2017 | During |
| 2009/0298892 A1 | 12/2009 | Nelson et al. |
| 2016/0346232 A1 | 12/2016 | During |
| 2017/0326200 A1 | 11/2017 | Danglas et al. |
| 2019/0298686 A1 * | 10/2019 | Burnett ............ A61K 31/366 |

FOREIGN PATENT DOCUMENTS

| | | |
|---|---|---|
| WO | 2010090737 A1 | 8/2010 |
| WO | 2012018059 A1 | 2/2012 |
| WO | 2012020780 A1 | 2/2012 |
| WO | 2015141662 A1 | 9/2015 |
| WO | 2016030345 A1 | 3/2016 |
| WO | 2017210540 A1 | 12/2017 |

OTHER PUBLICATIONS

Harada et al., "Characterization of Binding and Inhibitory Properties of TAK-063, a Novel Phosphodiesterase 10A Inhibitor," PLoS One, vol. 10, Issue 3, Mar. 27, 2015; pp. 1-15.

Suzuki et al., "In Vivo Pharmacological Characterization of TAK-063, a Potent and Selective Phosphodiesterase 10A Inhibitor with Antipsychotic-Like Activity in Rodents," Journal of Pharmacology and Experimental Therapeutics, vol. 352, Issue 3, Mar. 2015; pp. 471-479.

Kunitomo et al., "Discovery of 1-[2-Fluoro-4-(1H-pyrazol-1-yl)phenyl]-5-methoxy-3-(1-phenyl-1H-pyrazol-5-yl) pyridazin-4(1H)-one (TAK-063), a Highly Potent, Selective, and Orally Active Phosphodiesterase 10A (PDE10A) Inhibitor," Journal of Medicinal Chemistry, vol. 57, Issue 22, (2014); pp. 9627-9643.

International Search Report and the Written Opinion of the International Searching Authority, dated May 1, 2019, corresponding to counterpart International Application No. PCT/US19/18193; 17 total pages.

Nishi et al., "Distinct Roles of PDE4 and PDE10A in the Regulation of cAMP/PKA Signaling in the Striatum," The Journal of Neuroscience, Oct. 15, 2018, vol. 28, No. 42; pp. 10460-10471.

* cited by examiner

*Primary Examiner* — Raymond J Henley, III

(74) *Attorney, Agent, or Firm* — Carter, DeLuca & Farrell LLP

(57) ABSTRACT

Methods of treating developmental syndromes with a PDE10A inhibitor are provided.

8 Claims, No Drawings

METHODS OF TREATING DEVELOPMENTAL SYNDROMES WITH PDE10A INHIBITORS

CROSS-REFERENCE TO RELATED APPLICATION

This application claims benefit of and priority to U.S. Provisional Application No. 62/631,077, filed Feb. 15, 2018, which is incorporated herein by reference in its entirety.

TECHNICAL FIELD

Methods of treating developmental syndromes with a PDE10A inhibitor.

BACKGROUND

PDE10A is of the known 12 families of phosphodiesterases, the one with the most restricted expression, largely confined to the brain. It is a dual specificity enzyme with both cAMP and cGMP as substrates. As such, PDE10A inhibition increases the levels of both these second messengers and therefore augments receptors and signaling positively coupled to either PKA or PKG. The functional consequences of such inhibition are dependent on both the expression pattern or localization of the enzyme, as well as the activity of the relevant network of neurons. As PDE10A expression is most highly expressed in the caudate and putamen (also referred to as the striatum in lower species), the emphasis of the vast majority of investigators has been on the effect of PDE10A inhibition in disorders with altered caudate/putamen function, specifically schizophrenia and Huntington's Disease (HD). The enzyme is however more widely expressed, including cortex, hippocampus, prefrontal cortex and outside the CNS, the testis.

Developmental syndromes range in severity and include disorders such as Prader-Willi syndrome, 16p11.2 deletion syndrome, 16p11.2 recurrent microdeletion, Albright hereditary osteodystrophy, Alstrom syndrome, Bardet-Biedl syndrome, Borjeson-Forssman-Lehmann syndrome, Cohen syndrome, fragile X syndrome, fragile X syndrome (Prader-Willi Subtype), Down syndrome, Klinefelter syndrome, Turner syndrome, Smith-Magenis syndrome, Angelman syndrome, 21-Hydroxylase-Deficient Congenital Adrenal Hyperplasia, 2q37 Microdeletion syndrome, 3q29 Recurrent Deletion, Achondroplasia, ADNP-Related Intellectual Disability and Autism Spectrum Disorder and melanocortin 4 receptor (MC4R) deficiency. For example, Prader-Willi syndrome (PWS) is a genetic disease caused by lack of expression of genes from an imprinted region of the paternally inherited chromosome 15q11-q13, near the centromere (Aycan and Bas, *J Clin Res Pediatr Endocrinol*, 6(2):62-67 (2014)). The frequency of the disease is between about 1/10,000 and 1/30,000 with approximately 400,000 PWS patients living worldwide. PWS is a spectrum disorder which affects many systems in the body. Subjects with PWS typically suffer from a host of symptoms including neurologic, cognitive, endocrine, and behavioral abnormalities. Initially, infants exhibit hypotonia (floppy baby syndrome) and experience difficulty in sucking and feeding which can lead to growth delay. Subjects with PWS frequently have poor muscle tone, growth hormone deficiency, low levels of sex hormones, a constant feeling of hunger and excessive appetite (hyperphagia). They overeat, leading to weight gain, obesity and a high incidence of diabetes. Other signs appear including short stature, poor motor skills, underdeveloped sex organs, and mild intellectual and learning disabilities. PWS subjects may experience delayed speech and language development, and infertility. Behavioral symptoms may include cognitive impairment, cognitive rigidity, emotional lability and obsessive-compulsive behavior, with autistic symptomology, psychotic episodes, and biopolar disorder with psychosis. Additional clinical manifestations may include excessive daytime sleepiness, scoliosis, osteopenia/osteoporosis, decreased gastrointestinal motility, sleep disturbances, and reduced pain sensitivity.

There remains a need for methods for treating developmental syndromes.

SUMMARY

Methods of treating developmental syndromes with a PDE10A inhibitor are provided. In embodiments, the methods include treating a developmental syndrome including Prader-Willi syndrome, 16p11.2 deletion syndrome, 16p11.2 recurrent microdeletion, Albright hereditary osteodystrophy, Alstrom syndrome, Bardet-Biedl syndrome, Borjeson-Forssman-Lehmann syndrome, Cohen syndrome, fragile X syndrome, fragile X syndrome (Prader-Willi Subtype), Down syndrome, Klinefelter syndrome, Turner syndrome, Smith-Magenis syndrome, Angelman syndrome, 21-Hydroxylase-Deficient Congenital Adrenal Hyperplasia, 2q37 Microdeletion syndrome, 3q29 Recurrent Deletion, Achondroplasia, ADNP-Related Intellectual Disability and Autism Spectrum Disorder and melanocortin 4 receptor (MC4R) deficiency.

In embodiments, the methods include administering a PDE10A inhibitor including 1-[2-fluoro-4-(1H-pyrazol-1-yl)phenyl]-5-methoxy-3-(1-phenyl-1H-pyrazol-5-yl)-pyridazin-4(1H)-one, 1-(4-(3-(4-(1H-Benzo[d]imidazole-2-carbonyl)phenoxy)pyrazin-2-yl)piperidin-1-yl)ethanone, 2-[4-(1-Methyl-4-pyridin-4-yl-1H-pyrazol-3-yl)-phenoxymethyl]-quinoline, and 6-chloro-N-((2,4-dimethylthiazol-5-yl)methyl)-5-methyl-2-(3-(quinolin-2-yl)propoxy)pyrimidin-4-amine.

In embodiments, a composition including from 0.1 mg to 1500 mg of a PDE10A inhibitor or a pharmaceutically acceptable salt thereof is administered within a 24-hour period.

In embodiments, a composition including a PDE10A inhibitor or a pharmaceutically acceptable salt thereof is administered from one to four times a day. In embodiments, administering a composition including a PDE10A inhibitor or pharmaceutically acceptable salt thereof is accomplished via one or more of the following routes: oral, buccal, sublingual, rectal, topical, intranasal, vaginal, and parenteral. In embodiments, administering a composition including a PDE10A inhibitor or a pharmaceutically acceptable salt thereof provides improvement in at least one of the following symptoms: hypotonia, difficulty in sucking, difficulty in feeding, poor muscle tone, growth hormone deficiency, low levels of sex hormones, a constant feeling of hunger, excessive appetite (hyperphagia), weight gain, obesity, short stature, poor motor skills, underdeveloped sex organs, intellectual disability, learning disability, delayed speech development, delayed language development, infertility, cognitive impairment, cognitive rigidity, emotional lability, self-injury, obsessive-compulsive behavior, autistic symptomology, psychotic episodes, bipolar disorder with psychosis, excessive daytime sleepiness, scoliosis, osteope-

DETAILED DESCRIPTION

Described herein are methods and compositions for treating a developmental syndrome with a PDE10a inhibitor. Developmental disorders described herein include Prader-Willi syndrome, 16p11.2 deletion syndrome, 16p11.2 recurrent microdeletion, Albright hereditary osteodystrophy, Alstrom syndrome, Bardet-Biedl syndrome, Borjeson-Forssman-Lehmann syndrome, Cohen syndrome, fragile X syndrome, fragile X syndrome (Prader-Willi Subtype), Down syndrome, Klinefelter syndrome, Turner syndrome, Smith-Magenis syndrome, Angelman syndrome, 21-Hydroxylase-Deficient Congenital Adrenal Hyperplasia, 2q37 Microdeletion syndrome, 3q29 Recurrent Deletion, Achondroplasia, ADNP-Related Intellectual Disability and Autism Spectrum Disorder and melanocortin 4 receptor (MC4R) deficiency. PDE10a inhibitors include 1-[2-fluoro-4-(1H-pyrazol-1-yl)phenyl]-5-methoxy-3-(1-phenyl-1H-pyrazol-5-yl)-pyridazin-4(1H)-one, 1-(4-(3-(4-(1H-Benzo[d]imidazole-2-carbonyl)phenoxy)pyrazin-2-yl)piperidin-1-yl)ethanone, 2-[4-(1-Methyl-4-pyridin-4-yl-1H-pyrazol-3-yl)-phenoxymethyl]-quinoline, 6-chloro-N-((2,4-dimethylthiazol-5-yl)methyl)-5-methyl-2-(3-(quinolin-2-yl)propoxy)pyrimidin-4-amine.

Other PDE10a inhibitors that may be used in the methods and compositions for treating a development syndrome will be apparent to one skilled in the art. For example, PDE10A inhibitors are described in Hu et al., J. Med. Chem. 2014, 57, 6632-6641; Buijnsters et al., ACS Med. Chem. Lett. 2014, 5, 1049-1053; Shipe et al., J. Med. Chem. 2015, 58, 7888-7894, the disclosures of which are incorporated herein in their entirety.

In embodiments, provided are methods and compositions for treating developmental syndrome by administering to a subject in need thereof a pharmaceutical composition including an effective amount of 1-[2-fluoro-4-(1H-pyrazol-1-yl)phenyl]-5-methoxy-3-(1-phenyl-1H-pyrazol-5-yl)-pyridazin-4(1H)-one or a pharmaceutically acceptable salt thereof.

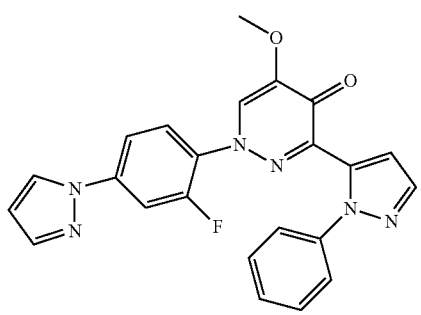 [SMILES: COc1cn(-c2ccc(-n3cccn3)cc2F)nc(-c2ccnn2-c2ccccc2)c1=O]

In embodiments, provided are methods and compositions for treating developmental syndrome by administering to a subject in need thereof a pharmaceutical composition including an effective amount of 1-(4-(3-(4-(1H-Benzo[d]imidazole-2-carbonyl)phenoxy)pyrazin-2-yl)piperidin-1-yl)ethanone or a pharmaceutically acceptable salt thereof.

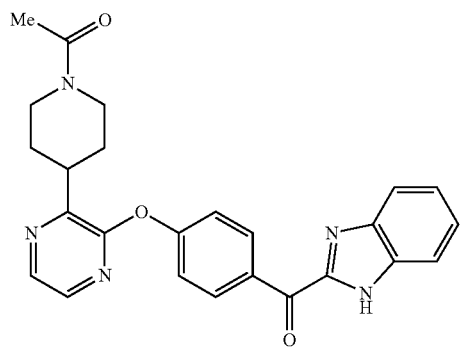 [SMILES: CC(=O)N1CCC(c2nccnc2Oc2ccc(C(=O)c3nc4ccccc4[nH]3)cc2)CC1]

In embodiments, provided are methods and compositions for treating developmental syndrome by administering to a subject in need thereof a pharmaceutical composition including an effective amount of 2-[4-(1-Methyl-4-pyridin-4-yl-1H-pyrazol-3-yl)-phenoxymethyl]-quinoline or a pharmaceutically acceptable salt thereof.

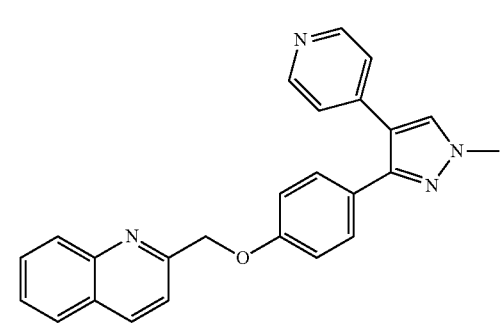 [SMILES: Cn1cc(-c2ccncc2)c(-c2ccc(OCc3ccc4ccccc4n3)cc2)n1]

In embodiments, provided are methods and compositions for treating developmental syndrome by administering to a subject in need thereof a pharmaceutical composition including an effective amount of 6-chloro-N-((2,4-dimethylthiazol-5-yl)methyl)-5-methyl-2-(3-(quinolin-2-yl)propoxy)pyrimidin-4-amine or a pharmaceutically acceptable salt thereof.

In embodiments, provided are methods and compositions for treating Prader-Willi syndrome by administering to a subject in need thereof a pharmaceutical composition including an effective amount of a PDE10A inhibitor. In some examples, the PDE10A inhibitor is 1-[2-fluoro-4-(1H-pyrazol-1-yl)phenyl]-5-methoxy-3-(1-phenyl-1H-pyrazol-5-yl)-pyridazin-4(1H)-one or a pharmaceutically acceptable salt thereof.

Symptoms of Prader-Willi syndrome include hypotonia, difficulty in sucking, difficulty in feeding, poor muscle tone, growth hormone deficiency, low levels of sex hormones, a constant feeling of hunger, excessive appetite (hyperphagia), weight gain, obesity, short stature, poor motor skills, underdeveloped sex organs, intellectual disability, learning disability, delayed speech development, delayed language development, infertility, cognitive rigidity, cognitive impairment, emotional lability, obsessive-compulsive behavior, autistic symptomology, excessive daytime sleepiness, scoliosis, osteopenia/osteoporosis, decreased gastrointestinal motility, sleep disturbances, and/or reduced pain sensitivity. In addition, in approximately 10% of individuals with PWS, more severe psychiatric illness can result including psychotic episodes, depression and bipolar disorder with psychosis.

Criteria regarding learning disorders are provided in the DSM-5 that considers specific learning disabilities to be a type of neurodevelopmental disorder that impedes the ability to learn or use specific academic skills (e.g., reading, writing, or arithmetic), which are the foundation for other learning.

Cognitive impairment may be measured against normal cognitive function, which refers to the normal physiologic activity of the brain, including, but not limited to, one or more of the following: mental stability, memory/recall abilities, problem solving abilities, reasoning abilities, thinking abilities, judging abilities, ability to discriminate or make choices, capacity for learning, ease of learning, perception, intuition, attention, and awareness, as measured by any criteria suitable in the art.

Cognitive impairment also includes deficits in mental activities that are mild or that otherwise do not significantly interfere with daily life. Mild cognitive impairment (MCI) is an example of such a condition. A patient with mild cognitive impairment may display symptoms of dementia (e.g., difficulties with language or memory) but the severity of these symptoms is such that a diagnosis of dementia may not be appropriate.

One skilled in the art will appreciate that there are numerous human and animal models that may be used to evaluate and compare the relative safety and efficacy of the PDE10A inhibitors for the treatment of cognitive impairment. In humans, cognitive function may be measured, for example and without limitation, by the clinical global impression of change scale (CGI); the Mini Mental State Exam (MMSE) (aka the Folstein Test); the Neuropsychiatric Inventory (NPI); the Clinical Dementia Rating Scale (CDR); the Cambridge Neuropsychological Test Automated Battery (CANTAB), the Sandoz Clinical Assessment-Geriatric (SCAG) scale, the Benton Visual Retention Test (BVRT), Montreal Cognitive Assessment (MoCA) or Digit Symbol Substitution Test (DSST).

In animal model systems, cognitive function may be measured in various conventional ways known in the art, including using a Morris Water Navigation Task, Barnes maze, radial arm maze task, T maze and the like. Other tests known in the art may also be used to assess cognitive function, such as novel object recognition and odor recognition tasks.

Cognitive function may also be measured using imaging techniques such as Positron Emission Tomography (PET), functional magnetic resonance imaging (fMRI), Single Photon Emission Computed Tomography (SPECT), or any other imaging technique that allows one to measure brain function. In animals, cognitive function may also be measured with electrophysiological techniques.

Accordingly, a PDE10A inhibitor or a pharmaceutically acceptable salt thereof is used to treat a subject having Prader-Willi syndrome. The subject may be an animal, e.g., mammal, e.g., human, etc. As used herein, the terms "treat", "treatment" or "treating" encompass any manner in which the symptoms or pathology of a condition, disorder or disease associated with Prader-Willi syndrome are ameliorated or otherwise beneficially altered. In embodiments, "treat", "treatment" or "treating" can refer to inhibiting a disease or condition, e.g., arresting or reducing its development or at least one clinical or subclinical symptom thereof. In embodiments, "treat", "treatment" or "treating" can refer to relieving the disease or condition, e.g., causing regression of the disease or condition or at least one of its clinical or subclinical symptoms. In embodiments, "treating cognitive impairment" means ameliorating, beneficially altering and/or providing relief from one or more of the symptoms of cognitive impairment. The benefit to a subject being treated may be statistically significant, mathematically significant, or at least perceptible to the subject and/or the physician.

In embodiments, the terms "effective amount" or "therapeutically effective amount" refer to an amount of a compound, material, composition, medicament, or other material that is effective to achieve a particular pharmacological and/or physiologic effect in connection with PWS symptoms such as, but not limited to, one or more of the following: reducing or eliminating difficulty in sucking, reducing or eliminating difficulty in feeding, reducing or eliminating poor muscle tone, reducing or eliminating growth hormone deficiency, increasing levels of sex hormones, reducing or eliminating a constant feeling of hunger, reducing or eliminating excessive appetite (hyperphagia), reducing or eliminating weight gain, reducing or eliminating obesity, reducing or eliminating short stature, increasing motor skills, reducing or eliminating underdeveloped sex organs, reducing or eliminating intellectual disability, reducing or eliminating learning disability, reducing or eliminating delayed speech development, reducing or eliminating delayed language development, reducing or eliminating infertility, reducing or eliminating cognitive rigidity, reducing or eliminating cognitive impairment, reducing or eliminating emotional lability, reducing or eliminating obsessive-compulsive behavior, reducing or eliminating autistic symptomology, reducing or eliminating psychotic episodes, reducing or eliminating bipolar disorder with psychosis, reducing or eliminating excessive daytime sleepiness, reducing or eliminating scoliosis, reducing or eliminating osteopenia/osteoporosis, reducing or eliminating decreased gastrointestinal motility, reducing or eliminating sleep disturbances, and/or reducing or eliminating reduced pain sensitivity, enhancing cognitive function, increasing daytime activity, improving learning (either the rate or ease of learning), improving attention, improving social behavior, and/or improving cerebrovascular function.

In embodiments, effective amount refers to an amount which may be suitable to prevent a decline in any one or more of the above qualities, or, in embodiments, to improve any one or more of the above qualities, for example, constant feeling of hunger, excessive appetite (hyperphagia), weight gain, obesity, cognitive function or performance, learning rate or ability, problem solving ability, attention span and ability to focus on a task or problem, social behavior, and the like. In embodiments, an effective amount may be suitable to reduce either the extent or rate of decline in a subject's appetite dysregulation, weight loss, cognitive skills or functioning, and/or the effective amount may be suitable to delay the onset of such decline. In embodiments, an effective amount may increase hypothalamic BDNF expression. Such effectiveness may be achieved, for example, by administering compositions described herein to an individual or to a population. In embodiments, the reduction, or delay of such a decline, or the improvement in an individual or population can be relative to a cohort, e.g., a control subject or a cohort population that has not received the treatment, or been administered the composition or medicament.

The dosage amount can vary according to a variety of factors such as subject-dependent variables (e.g., age, immune system, health, etc.), the disease or disorder being treated, as well as the route of administration and the pharmacokinetics of the agent being administered.

In embodiments, methods include treating a developmental syndrome, e.g., PWS, by administering to a patient in need thereof a pharmaceutical composition including about 0.01 mg to about 1000 mg or to about 1500 mg of a compound of a PDE10A inhibitor (e.g., 1-[2-fluoro-4-(1H-pyrazol-1-yl)phenyl]-5-methoxy-3-(1-phenyl-1H-pyrazol-5-yl)-pyridazin-4(1H)-one or a pharmaceutically acceptable salt thereof). In embodiments, doses may be, e.g., in the range of about 0.1 to 1500 mg, 0.1 to 1250 mg, 0.1 to 1000 mg, 0.1 to 750 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 1 to 1500 mg, 1 to 1000 mg, 1 to 500 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 1500 mg, 5 to 1000 mg, 5 to 500 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 1500 mg, 10 to 1000 mg, 10 to 500 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 1500 mg, 15 to 1000 mg, 15 to 500 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 1500 mg, 20 to 1000 mg, 20 to 500 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 1500 mg, 25 to 1000 mg, 25 to 500 mg, 25 to 300 mg, 25 to 250 mg, 25 to 200 mg, 25 to 175 mg, 25 to 150 mg, 25 to 125 mg, 25 to 100 mg, 25 to 75 mg, 25 to 50 mg, 25 to 30 mg, 30 to 1500 mg, 30 to 1000 mg, 30 to 500 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 35 to 1500 mg, 35 to 1000 mg, 35 to 500 mg, 35 to 300 mg, 35 to 250 mg, 35 to 200 mg, 35 to 175 mg, 35 to 150 mg, 35 to 125 mg, 35 to 100 mg, 35 to 75 mg, 35 to 50 mg, 40 to 1500 mg, 40 to 1000 mg, 40 to 500 mg, 40 to 300 mg, 40 to 250 mg, 40 to 200 mg, 40 to 175 mg, 40 to 150 mg, 40 to 125 mg, 40 to 100 mg, 40 to 75 mg, 40 to 50 mg, 50 to 1500 mg, 50 to 1000 mg, 50 to 500 mg, 50 to 300 mg, 50 to 250 mg, 50 to 200 mg, 50 to 175 mg, 50 to 150 mg, 50 to 125 mg, 50 to 100 mg, 50 to 75 mg, 75 to 1500 mg, 75 to 1000 mg, 75 to 500 mg, 75 to 300 mg, 75 to 250 mg, 75 to 200 mg, 75 to 175 mg, 75 to 150 mg, 75 to 125 mg, 75 to 100 mg, 100 to 1500 mg, 100 to 1000 mg, 100 to 500 mg, 100 to 300 mg, 100 to 250 mg, 100 to 200 mg, 100 to 175 mg, 100 to 150 mg, 100 to 125 mg, 125 to 1500 mg, 125 to 1000 mg, 125 to 500 mg, 125 to 300 mg, 125 to 250 mg, 125 to 200 mg, 125 to 175 mg, 125 to 150 mg, 150 to 1500 mg, 150 to 1000 mg, 150 to 500 mg, 150 to 300 mg, 150 to 250 mg, 150 to 200 mg, 150 to 175 mg, 175 to 1500 mg, 175 to 1000 mg, 175 to 500 mg, 175 to 300 mg, 175 to 250 mg, 175 to 200 mg, 200 to 1500 mg, 200 to 1000 mg, 200 to 500 mg, 200 to 300 mg, 200 to 250 mg, 250 to 1500 mg, 250 to 1000 mg, 250 to 500 mg, 250 to 300 mg, 7.5 to 15 mg, 2.5 to 5 mg, 1 to 5 mg, with doses of, e.g., about 0.25 mg, 0.5 mg, 0.75 mg, 1 mg, 1.25 mg, 1.5 mg, 1.75 mg, 2.0 mg, 2.5 mg, 3.0 mg, 3.5 mg, 4.0 mg, 4.5 mg, 5 mg, 10 mg, 15 mg, 20 mg, 25 mg, 30, mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions may include a PDE10A inhibitor (e.g., 1-[2-fluoro-4-(1H-pyrazol-1-yl)phenyl]-5-methoxy-3-(1-phenyl-1H-pyrazol-5-yl)- pyridazin-4(1H)-one or a pharmaceutically acceptable salt thereof) in an amount of, e.g., about 0.01 to 500 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.1 mg, 0.25 mg, 0.5 mg, 0.75 mg, 1 mg, 3 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1025 mg, 1050 mg, 1075 mg, 1100 mg, 1125 mg, 1150 mg, 1175 mg, 1200 mg, 1225 mg, 1250 mg, 1275 mg, 1300 mg, 1325 mg, 1350 mg, 1375 mg, 1400 mg, 1425 mg, 1450 mg, 1475 mg, and 1500 mg being examples.

Typically, dosages may be administered to a subject once, twice, three or four times daily, every other day, once weekly, or once a month. In embodiments, a PDE10A inhibitor (e.g., 1-[2-fluoro-4-(1H-pyrazol-1-yl)phenyl]-5- methoxy-3-(1-phenyl-1H-pyrazol-5-yl)-pyridazin-4(1H)-one or a pharmaceutically acceptable salt thereof) is administered to a subject once in the morning, or once in the evening. In embodiments, a PDE10A inhibitor (e.g., 1-[2-fluoro-4-(1H-pyrazol-1-yl)phenyl]-5-methoxy-3-(1-phenyl-1H-pyrazol-5-yl)-pyridazin-4(1H)-one or a pharmaceutically acceptable salt thereof) is administered to a subject once in the morning, and once in the evening. In embodiments, a PDE10A inhibitor (e.g., 1-[2-fluoro-4-(1H-pyrazol-1-yl)phenyl]-5-methoxy-3-(1-phenyl-1H-pyrazol-5-yl)-pyridazin-4(1H)-one or a pharmaceutically acceptable salt thereof) is administered to a subject three times a day (e.g., at breakfast, lunch, and dinner), at a dose, e.g., of 50 mg/administration (e.g., 150 mg/day).

In embodiments, a PDE10A inhibitor (e.g., 1-[2-fluoro-4-(1H-pyrazol-1-yl)phenyl]-5-methoxy-3-(1-phenyl-1H-pyrazol-5-yl)-pyridazin-4(1H)-one or a pharmaceutically acceptable salt thereof) is administered to a subject 50 mg/per day in one or more doses. In embodiments, a PDE10A inhibitor (e.g., 1-[2-fluoro-4-(1H-pyrazol-1-yl)phenyl]-5-methoxy-3-(1-phenyl-1H-pyrazol-5-yl)-pyridazin-4(1H)-one or a pharmaceutically acceptable salt thereof) is administered to a subject 100 mg/per day in one or more doses. In embodiments, a PDE10A inhibitor (e.g., 1-[2-fluoro-4-(1H-pyrazol-1-yl)phenyl]-5-methoxy-3-(1-phenyl-1H-pyrazol-5-yl)-pyridazin-4(1H)-one or a pharmaceutically acceptable salt thereof) is administered to a subject 200 mg/per day in one or more doses. In embodiments, a PDE10A inhibitor (e.g., 1-[2-fluoro-4-(1H-pyrazol-1-yl)phenyl]-5-methoxy-3-(1-phenyl-1H-pyrazol-5-yl)-pyridazin-4(1H)-one or a pharmaceutically acceptable salt thereof) is administered to a subject 300 mg/per day in one or more doses. In embodiments, a PDE10A inhibitor (e.g., 1-[2-fluoro-4-(1H-pyrazol-1-yl)phenyl]-5-methoxy-3-(1-phenyl-1H-pyrazol-5-yl)-pyridazin-4(1H)-one or a pharmaceutically acceptable salt thereof) is administered to a subject 400 mg/per day in one or more doses. In embodiments, a PDE10A inhibitor (e.g., 1-[2-fluoro-4-(1H-pyrazol-1-yl)phenyl]-5-methoxy-3-(1-phenyl-1H-pyrazol-5-yl)-pyridazin-4(1H)-one or a pharmaceutically acceptable salt thereof) is administered to a subject 500 mg/per day in one or more doses. In embodiments, a PDE10A inhibitor (e.g., 1-[2-fluoro-4-(1H-pyrazol-1-yl)phenyl]-5-methoxy-3-(1-phenyl-1H-pyrazol-5-yl)-pyridazin-4(1H)-one or a pharmaceutically acceptable salt thereof) is administered to a subject 1000 mg/per day in one or more doses.

In embodiments, the dosage of a PDE10A inhibitor (e.g., 1-[2-fluoro-4-(1H-pyrazol-1-yl)phenyl]-5-methoxy-3-(1-phenyl-1H-pyrazol-5-yl)-pyridazin-4(1H)-one or a pharmaceutically acceptable salt thereof) is 0.01-100 mg/kg, 0.5-50 mg/kg, 0.5-10 mg/kg or 25-50 mg/kg once, twice, three times or four times daily. For example, in embodiments, the dosage is 0.5 mg/kg, 1 mg/kg, 5 mg/kg, 7.5 mg/kg, or 10 mg/kg once, twice, three times or four times daily. In embodiments, a subject is administered a total daily dose of 0.01 mg to 1500 mg of a PDE10A inhibitor (e.g., 1-[2-fluoro-4-(1H-pyrazol-1-yl)phenyl]-5-methoxy-3-(1-phenyl-1H-pyrazol-5-yl)-pyridazin-4(1H)-one or a pharmaceutically acceptable salt thereof) once, twice, three times, four times daily. In embodiments, the total amount administered to a subject in 24-hour period is, e.g., 5 mg, 10 mg, 20 mg, 25 mg, 30 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1025 mg, 1050 mg, 1075 mg, 1100 mg, 1125 mg, 1150 mg, 1175 mg, 1200 mg, 1225 mg, 1250 mg, 1275 mg, 1300 mg, 1325 mg, 1350 mg, 1375 mg, 1400 mg, 1425 mg, 1450 mg, 1475 mg, or 1500 mg. In embodiments, the subject may be started at a low dose and the dosage is escalated. In embodiments, the subject may be started at a high dose and the dosage is decreased.

Suitable dosage forms for a PDE10A inhibitor (e.g., 1-[2-fluoro-4-(1H-pyrazol-1-yl)phenyl]-5-methoxy-3-(1-phenyl-1H-pyrazol-5-yl)-pyridazin-4(1H)-one or a pharmaceutically acceptable salt thereof) include, but are not limited to oral forms, such as tablets, hard or soft gelatin capsules, powders, granules and oral solutions, syrups or suspensions, troches, as well as the sublingual, buccal, intratracheal, intraocular, intranasal forms, forms adapted to inhalation, topical, transdermal, rectal forms such as suppositories, and implants for release of medication, parenteral forms, for example, intravenous, intra-arterial, intraperitoneal, intrathecal, intraventricular, intraurethrally, intrasternal, intracranial, intramuscularly or subcutaneously. In embodiments, for such parenteral administration, it may be in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Pharmaceutical compositions herein may be provided with immediate release, delayed release, extended release, or modified release profiles. In embodiments, a delayed release dosage form is one that releases a drug (or drugs) at a time other than promptly after administration. In embodiments, an extended release dosage form is one that allows at least a twofold reduction in dosing frequency as compared to that drug presented as a conventional dosage form (e.g. as a solution or prompt drug-releasing, conventional solid dosage form). In embodiments, a modified release dosage form is one for which the drug release characteristics of time course and/or location are chosen to accomplish therapeutic or convenience objectives not offered by conventional dosage forms such as solutions, ointments, or promptly dissolving dosage forms. Delayed release and extended release dosage forms and their combinations may be considered as types of modified release dosage forms.

In embodiments, pharmaceutical compositions with different drug release profiles may be combined to create a two-phase or three-phase release profile. For example, pharmaceutical compositions may be provided with an immediate release and an extended release profile. In embodiments, pharmaceutical compositions may be provided with an extended release and delayed release profile. Such composition may be provided as pulsatile formulations, multilayer tablets, or capsules containing tablets, beads, granules, etc. Compositions may be prepared using a pharmaceutically acceptable "carrier" composed of materials that are considered safe and effective. The "carrier" includes all components present in the pharmaceutical formulation other than the active ingredient or ingredients. The term "carrier" includes, but is not limited to, diluents, binders, lubricants, glidants, disintegrants, fillers, and coating compositions.

As used herein, the term "pharmaceutically acceptable" refers to molecular entities and compositions that are "generally regarded as safe", e.g., that are physiologically tolerable and do not typically produce an allergic or similar untoward reaction when administered to a human. In embodiments, this term refers to molecular entities and compositions approved by a regulatory agency of the federal or a state government, as the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

As used herein, the term "pharmaceutically acceptable salts" includes acid addition salts, addition salts of free bases, wherein the compound is modified by making acid or base salts thereof. Examples of pharmaceutically acceptable salts include but are not limited to mineral or organic acid salts of basic residues such as amines, and alkali or organic salts of acidic residues such as carboxylic acids. Pharmaceutically acceptable salts include conventional non-toxic salts or quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, and oxalic salts. In embodiments, a PDE10A inhibitor (e.g., 1-[2-fluoro-4-(1H-pyrazol-1-yl)phenyl]-5-methoxy-3-(1-phenyl-1H-pyrazol-5-yl)-pyridazin-4(1H)-one or pharmaceutically acceptable salts thereof may include a hemifumarate salt. The pharmaceutically acceptable salts of a compound of the PDE10A inhibitors can be synthesized from the parent compound, which contains a basic or acidic moiety, by conventional chemical methods.

The terms "about" or "approximately" as used herein mean within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, a range up to 10%, a range up to 5%, and/or a range up to 1% of a given value. Alternatively, particularly with respect to biological systems or processes, the term can mean within an order of magnitude, e.g., within 5-fold, or within 2-fold, of a value. "About" and "approximately" are used interchangeably herein.

The PDE10A inhibitor (e.g., 1-[2-fluoro-4-(1H-pyrazol-1-yl)phenyl]-5-methoxy-3-(1-phenyl-1H-pyrazol-5-yl)-pyridazin-4(1H)-one or a pharmaceutically acceptable salt thereof) may be racemic and/or optically active isomers thereof. In this regard, some of the compounds can have asymmetric carbon atoms, and therefore, can exist either as racemic mixtures or as individual optical isomers (enantiomers). Compounds described herein that contain a chiral center include all possible stereoisomers of the compound, including compositions including the racemic mixture of the two enantiomers, as well as compositions including each enantiomer individually, substantially free of the other enantiomer. Thus, for example, contemplated herein is a composition including the S enantiomer of a compound substantially free of the R enantiomer, or the R enantiomer substantially free of the S enantiomer. If the named compound includes more than one chiral center, the scope of the present disclosure also includes compositions including mixtures of varying proportions between the diastereomers, as well as compositions including one or more diastereomers substantially free of one or more of the other diastereomers. By "substantially free" it is meant that the composition includes less than 25%, 15%, 10%, 8%, 5%, 3%, or less than 1% of the minor enantiomer or diastereomer(s).

Methods for synthesizing, isolating, preparing, and administering various stereoisomers are known in the art. Separation of diastereoisomers or cis and trans isomers may be achieved by conventional techniques, such as, for example, by fractional crystallisation, chromatography or High Performance Liquid Chromatography (HPLC) of a stereoisomeric mixture of the agent or a suitable salt or derivative thereof. An individual enantiomer of a compound of a PDE10A inhibitor may also be prepared from a corresponding optically pure intermediate or by resolution, such as by HPLC of the corresponding racemate using a suitable chiral support or by fractional crystallisation of the diastereoisomeric salts formed by reaction of the corresponding racemate with a suitable optically active acid or base, as appropriate.

The following examples are included to augment the disclosure herein and should not be construed as limiting in any sense.

EXAMPLES

Example 1

Assessment of Safety, Tolerability, Pharmacokinetics and Pharmacodynamics of 1-[2-fluoro-4-(1H-pyrazol-1-yl)phenyl]-5-methoxy-3-(1-phenyl-1H-pyrazol-5-yl)-pyridazin-4(1H)-one In this study, conducted by Tsai, et al., Psychopharmacology (2116) 233:3787-3795, volunteers were randomized into 1 of 6 dose cohorts of 3, 10, 30, 100, 300, and 1000 mg of 1-[2-fluoro-4-(1H-pyrazol-1-yl)phenyl]-5-methoxy-3-(1-phenyl-1H-pyrazol-5-yl)-pyridazin-4(1H)-one. Each fasting volunteer randomly received a single dose of 1-[2-fluoro-4-(1H-pyrazol-1-yl)phenyl]-5-methoxy-3-(1-phenyl-1H-pyrazol-5-yl)-pyridazin-4(1H)-one or placebo. Individuals from the 100-mg cohort also received a post-washout, 100-mg dose under fed conditions. A total of 84 volunteers enrolled (14 per cohort).

Laboratory tests evaluated hematology, serum chemistry, urine, and hormone levels. Serial plasma and urine samples were collected from all subjects prior to dosing and at specific time points or intervals up to 96 h postdose. Pharmacokinetic samples were processed immediately and frozen at −20° C. as duplicate sets. Plasma concentrations of 1-[2-fluoro-4-(1H-pyrazol-1-yl)phenyl]-5-methoxy-3-(1-phenyl-1H-pyrazol-5-yl)-pyridazin-4(1H)-one were subsequently measured by validated liquid chromatography-tandem mass spectrometry with a validated range of 0.5 to 1000 ng/mL. The PK parameters analyzed for 1-[2-fluoro-4-(1H-pyrazol-1-yl)phenyl]-5-methoxy-3-(1-phenyl-1H-pyrazol-5-yl)-pyridazin-4(1H)-one in plasma and urine included area under the plasma concentration-time curve from time 0 to infinity ($AUC_{(0-inf)}$), maximum observed plasma concentration ($C_{max}$), time to reach $C_{max}$ ($T_{max}$), terminal elimination half-life ($T_{1/2}$), oral clearance (CL/F), volume of distribution ($V_z/F$), and renal clearance ($CL_r$). Metabolite-to-parent ratios were estimated from $C_{max}$ and $AUC_{(0-inf)}$ data. The PK parameters were derived using non-compartmental methods with WinNonlin Enterprise Version 6.3 (Pharsight Corp., Mountain View, Calif., USA). Under fasting conditions, 1-[2-fluoro-4-(1H-pyrazol-1-yl)phenyl]-5-methoxy-3-(1-phenyl-1H-pyrazol-5-yl)-pyridazin-4(1H)-one was absorbed with a median $T_{max}$ value of 3 to 4 h postdose and eliminated with a mean $T_{1/2}$ value of 15 to 25 h postdose across all subjects. Fed conditions slowed absorption ($T_{max}$=6 h) and increased oral bioavailability.

The most common drug-related adverse events were somnolence (33.3%), orthostatic tachycardia (19.7%), and orthostatic hypotension (9.1%). The three severe adverse events recorded occurred at the highest doses: orthostatic hypotension (n=1; 300 mg) and somnolence (n=2; 1000 mg). There were no deaths, serious adverse events, or discontinuations due to adverse events.

Example 2

Prospective Assessment of the Safety and Efficacy of 1-[2-fluoro-4-(1H-pyrazol-1-yl)phenyl]-5-methoxy-3-(1-phenyl-1H-pyrazol-5-yl)-pyridazin-4(1H)-one in Ghrelin Suppression in Individuals with Prader-Willi Syndrome The purpose of this study is to evaluate the effect of 1-[2-fluoro-4-(1H-pyrazol-1-yl)phenyl]-5-methoxy-3-(1-phenyl-1H-pyrazol-5-yl)-pyridazin-4(1H)-one on levels of ghrelin, hunger, and body weight in people with Prader-Willi syndrome. This study will be a multi-center, randomized, placebo-controlled, double blind trial in which patients meeting entrance criteria will be randomly assigned to receive placebo or active drug. Enrolled subjects will have diagnosis of PWS confirmed by chromosome analysis (i.e. interstitial deletion of paternally-derived chromosome 15Q, uniparental maternal disomy or other chromosome 15 abnormalities), be 18 years and older, and have free T4, TSH values in the normal range (with or without thyroxine replacement). Subjects with confirmed hypogonadism who are corrected with adequate doses of sex steroid replacement, will have been treated for at least 6 months prior to entry and have no change in dosages over the study period. Patients with confirmed growth hormone deficiency who are corrected with adequate doses of replacement, will have been treated for at least 6 months prior to entry and have no change in dosages over the study period.

After baseline tests, subjects will be administered 1-[2-fluoro-4-(1H-pyrazol-1-yl)phenyl]-5-methoxy-3-(1-phenyl-1H-pyrazol-5-yl)-pyridazin-4(1H)-one or placebo for 6 months. At the end of this initial 6-month treatment period and a 4-month washout period, study subjects will then crossover to receive the alternative therapy (placebo or 1-[2-fluoro-4-(1H-pyrazol-1-yl)phenyl]-5-methoxy-3-(1-phenyl-1H-pyrazol-5-yl)-pyridazin-4(1H)-one) for an additional 6 months. Subjects will be followed for 16 months total at scheduled visits: 0, 2, 6, 10, 12, and 16 months. During each of these visits, testing will include measuring how well glucose (sugar) is processed, how much energy is burned off as heat, their amount of body fat, levels of the hormone ghrelin, and how much food is eaten at a meal. During these study periods participants will return monthly for physical examination and blood draw to check liver enzymes. Primary outcome measures are ghrelin levels (change from baseline to 6 months), appetite (change from baseline to 6 months), and body weight (change from baseline to 6 months). Secondary outcome measures are hormone levels (change from baseline to 6 months), body composition (change from baseline to 6 months), energy expenditure (change from baseline to 6 months), and glucose metabolism (change from baseline to 6 months).

Example 3

Prospective Assessment of the Effect of 1-[2-fluoro-4-(1H-pyrazol-1-yl)phenyl]-5-methoxy-3-(1-phenyl-1H-pyrazol-5-yl)-pyridazin-4(1H)-one on Weight Gain and Body Composition in Adults with Prader-Willi Syndrome The purpose of this study will be to evaluate the effect of 1-[2-fluoro-4-(1H-pyrazol-1-yl)phenyl]-5-methoxy-3-(1-phenyl-1H-pyrazol-5-yl)-pyridazin-4(1H)-one on the appetite, body weight, body fat and growth hormone level of subjects with PWS. This will be a double blind placebo controlled clinical trial involving a total of 18 young adults aged 18 to 35 years with PWS. Subjects will be selected if they have Prader Willi syndrome previously confirmed by standard genetic testing (the DNA methylation test) or meet the clinical diagnostic criteria as follows: the presence of at least four of the six principal characteristics of PWS syndrome including 1) infantile hypotonia, 2) abnormal pubertal development, 3) obesity after early infancy, 4) dysfunctional central nervous system performance, 5) dysmorphic facial features, and 6) short stature. In addition, they must have one or more of the following characteristics commonly associated with PWS: 1) small hands and feet, 2) skin problems, 3) behavioral problems related to food, and 4) decreased pain sensitivity. Subjects must have a BMI of at least 30 or more. Subjects will be divided in to the two groups of control and intervention, and treated with either placebo (inactive drug), or 1-[2-fluoro-4-(1H-pyrazol-1-yl)phenyl]-5-methoxy-3-(1-phenyl-1H-pyrazol-5-yl)-pyridazin-4(1H)-one for a total duration of 6 months. Body weight, fat distribution, objective and subjective assessment of the hunger, fasting blood sample for measurement of ghrelin and leptin, serum lipids, IGF-1 (growth hormone related protein), insulin and glucose concentrations will be measured upon enrollment, at 3 months, and at the end of the study. The proportion of body fat to muscle will be determined using a radiological technique, whole body dual-energy x-ray absorptiometry (DEXA) scan, and also by measurement of skin fold thickness, waist and hip circumference at the enrollment prior to the intervention, and at the end of the study.

Example 4

Prospective Assessment of the Effect of 1-[2-fluoro-4-(1H-pyrazol-1-yl)phenyl]-5-methoxy-3-(1-phenyl-1H-pyrazol-5-yl)-pyridazin-4(1H)-one on Self-Injurious Behavior in Adults With Prader-Willi Syndrome Prader-Willi syndrome may be characterized by a persistent pattern of self-injurious behavior (SIB), most notably skin picking, that results in frequent medical care and attention. SIB in mental retardation and related developmental disabilities is often monitored by behavioral observation methods. Direct evaluation of skin lesions has been reported to help systematically follow wounds and wound healing. The goal of this study is to characterize SIB in PWS and to evaluate the efficacy of 1-[2-fluoro-4-(1H-pyrazol-1-yl)phenyl]-5-methoxy-3-(1-phenyl-1H-pyrazol-5-yl)-pyridazin-4(1H)-one versus placebo in attenuating SIB in individuals with PWS.

This will be a double blind placebo controlled clinical trial involving adults aged 18 to 66 years with PWS. Subjects will be selected if they have Prader-Willi syndrome previously confirmed due to deletion of 15 q11-13 or uniparental disomy and are actively engaging skin picking behavior. Participants in the study will be randomized to receive either 1-[2-fluoro-4-(1H-pyrazol-1-yl)phenyl]-5-methoxy-3-(1-phenyl-1H-pyrazol-5-yl)-pyridazin-4(1H)-one or a placebo for 6 weeks. All participants will be monitored for SIB by observation and photographic recordings of the resultant skin lesions, by reports of group home staff, and by standardized rating measurements of self-injury. At the end of 6 weeks, participants receiving 1-[2-fluoro-4-(1H-pyrazol-1-yl)phenyl]-5-methoxy-3-(1-phenyl-1H-pyrazol-5-yl)-pyridazin-4(1H)-one will receive decreasing doses of 1-[2-fluoro-4-(1H-pyrazol-1-yl)phenyl]-5-methoxy-3-(1-phenyl-1H-pyrazol-5-yl)-pyridazin-4(1H)-one; participants receiving placebo will continue to receive the placebo. At week 9, participants previously receiving 1-[2-fluoro-4-(1H-pyrazol-1-yl)phenyl]-5-methoxy-3-(1-phenyl-1H-pyrazol-5-yl)-pyridazin-4(1H)-one will be given placebo and participants previously receiving placebo will be given 1-[2-fluoro-4-(1H-pyrazol-1-yl)phenyl]-5-methoxy-3-(1-phenyl-1H-pyrazol-5-yl)-pyridazin-4(1H)-one. After 6 weeks, all participants will be entered into a 4-month open-label extension phase. Safety and efficacy measurements will be assessed during the 15 study visits; in the event of worsening SIB, the blind will be broken by the study's medical oversight physician and, if appropriate, the participant will be placed directly into the 4-month open-label extension phase.

Example 5

Prospective Assessment of the Effect of 1-[2-fluoro-4-(1H-pyrazol-1-yl)phenyl]-5-methoxy-3-(1-phenyl-1H-pyrazol-5-yl)-pyridazin-4(1H)-one Therapy on Developmental, Nutritional and Hormonal Regulation of Ghrelin in Children and Young Adults With Prader-Willi Syndrome The purpose of this study is to investigate, over a 6 month period, the effect of 1-[2-fluoro-4-(1H-pyrazol-1-yl)phenyl]-5-methoxy-3-(1-phenyl-1H-pyrazol-5-yl)-pyridazin-4(1H)-one therapy on food intake, sense of hunger, body weight, body composition, efficiency of burning calories, biomarkers of weight regulation and growth hormone markers in children and young Adults with PWS. This will be a double blind placebo controlled clinical trial involving subjects with a diagnosis of PWS confirmed by chromosome analysis, ages 5 years to 21 years, BMI for age greater-than or equal to 85th percentile, and free T4, thyroid stimulating hormone (TSH) values in the normal range (either endogenous or with thyroxine replacement).

Primary outcome measures are number of participants showing a decrease in fasting total ghrelin from baseline to 6 months of treatment with 1-[2-fluoro-4-(1H-pyrazol-1-yl)phenyl]-5-methoxy-3-(1-phenyl-1H-pyrazol-5-yl)-pyridazin-4(1H)-one or placebo, number of participants with a decrease in weight from baseline to 6 months of 1-[2-fluoro-4-(1H-pyrazol-1-yl)phenyl]-5-methoxy-3-(1-phenyl-1H-pyrazol-5-yl)-pyridazin-4(1H)-one or placebo therapy, number of participants with decreased BMI z-score from baseline to 6 months of 1-[2-fluoro-4-(1H-pyrazol-1-yl)phenyl]-5-methoxy-3-(1-phenyl-1H-pyrazol-5-yl)-pyridazin-4(1H)-one or placebo therapy, number of participants with decreased skin-fold measurements from baseline to 6 months of 1-[2-fluoro-4-(1H-pyrazol-1-yl)phenyl]-5-methoxy-3-(1-phenyl-1H-pyrazol-5-yl)-pyridazin-4(1H)-one or placebo therapy, number of participants with decrease in hunger and food intake measured by hunger and hyperphagia by questionnaires and parent-reported 72-hour food recall from baseline to 6 months of 1-[2-fluoro-4-(1H-pyrazol-1-yl)phenyl]-5-methoxy-3-(1-phenyl-1H-pyrazol-5-yl)-pyridazin-4(1H)-one or placebo therapy. Multiple questionnaires consisting of a battery of free text answer questions and food diaries are combined in order to make a behavioral assessment of the participants food state of hunger and food intake. There is no defined scale for this assessment. Each participants' responses and parent responses are combined. Additional primary outcome measures are number of participants with improved insulin regulation from baseline to 6 months of 1-[2-fluoro-4-(1H-pyrazol-1-yl)phenyl]-5-methoxy-3-(1-phenyl-1H-pyrazol-5-yl)-pyridazin-4(1H)-one or placebo therapy. Insulin regulation will be measured by immunochemiluminescent assay, number of participants with improved adiponectin regulation from baseline to 6 months of 1-[2-fluoro-4-(1H-pyrazol-1-yl)phenyl]-5-methoxy-3-(1-phenyl-1H-pyrazol-5-yl)-pyridazin-4(1H)-one or placebo therapy, number of participants with improved Leptin regulation from baseline to 6 months of 1-[2-fluoro-4-(1H-pyrazol-1-yl)phenyl]-5-methoxy-3-(1-phenyl-1H-pyrazol-5-yl)-pyridazin-4(1H)-one or placebo therapy, and number of participants with improved Peptide YY (PYY) regulation from baseline to 6 months of 1-[2-fluoro-4-(1H-pyrazol-1-yl)phenyl]-5-methoxy-3-(1-phenyl-1H-pyrazol-5-yl)-pyridazin-4(1H)-one or placebo therapy. Secondary outcome measures are number of participants with decreased body-composition as measured by air displacement plethysmography (BOD POD® body composition tracking system) from baseline to 6 months of 1-[2-fluoro-4-(1H-pyrazol-1-yl)phenyl]-5-methoxy-3-(1-phenyl-1H-pyrazol-5-yl)-pyridazin-4(1H)-one or placebo therapy, number of participants with decreased body-composition as measured by dual energy X-ray absorptiometry (DEXA) scan from baseline to 6 months of 1-[2-fluoro-4-(1H-pyrazol-1-yl)phenyl]-5-methoxy-3-(1-phenyl-1H-pyrazol-5-yl)-pyridazin-4(1H)-one or placebo therapy measured at months 0, 3, and 6, and resting energy expenditure as measured by indirect calorimetry at months 0, 3 and 6.

Example 6

Prospective study to assess the safety and/or efficacy of 1-[2-fluoro-4-(1H-pyrazol-1-yl)phenyl]-5-methoxy-3-(1-phenyl-1H-pyrazol-5-yl)-pyridazin-4(1H)-one for the treatment of Obsessive Compulsive Behavior The goal of this prospective trial is to obtain efficacy, safety, and tolerability data of 1-[2-fluoro-4-(1H-pyrazol-1-yl)phenyl]-5-methoxy-3-(1-phenyl-1H-pyrazol-5-yl)-pyridazin-4(1H)-one for the potential treatment of Obsessive Compulsive Behavior (OCD). This will be a randomized, double-blind, placebo-controlled study. Five dose levels will be examined, starting at the lowest, in each population with 10 participants in each dose level. These participants will be randomized to receive 1-[2-fluoro-4-(1H-pyrazol-1-yl)phenyl]-5-methoxy-3-(1-phenyl-1H-pyrazol-5-yl)-pyridazin-4(1H)-one (8 subjects) and placebo (2 subjects) once daily (QD) for 7 days. In total, approximately 60 participants will be enrolled in the study.

The daily dosage regimen of 1-[2-fluoro-4-(1H-pyrazol-1-yl)phenyl]-5-methoxy-3-(1-phenyl-1H-pyrazol-5-yl)-pyridazin-4(1H)-one will be administered orally via tablets to respective groups in amounts of 3 mg, 10 mg, 20 mg, 30 mg, and 100 mg for seven days. Participants may be evaluated using a Primary Outcome Measures of OCD severity by examining the change from baseline in the Yale-Brown Obsessive-Compulsive Scale (Y-BOCS) ratings of OCD severity each day following administration. The Yale-Brown Obsessive Compulsive Scale (Y-BOCS) assesses obsessive and compulsive symptom severity. Obsessions are rated on a scale from 0-20 and compulsions are rated on a scale of 0-20, for a total scale of 0-40. Scores on the obsessions scale and scores on the compulsions scale are summed to obtain the total score. The higher the score, the more severe the OCD.

It should be understood that the examples and embodiments provided herein are exemplary examples embodiments. Those skilled in the art will envision various modifications of the examples and embodiments that are consistent with the scope of the disclosure herein. Such modifications are intended to be encompassed by the claims.

What is claimed is:

1. A method of treating a developmental syndrome selected from the group consisting of Prader-Willi syndrome, 16p11.2 deletion syndrome, 16p11.2 recurrent microdeletion, Albright hereditary osteodystrophy, Alstrom syndrome, Bardet-Biedl syndrome, Borjeson-Forssman-Lehmann syndrome, Cohen syndrome, fragile X syndrome, fragile X syndrome (Prader-Willi Subtype), Down syndrome, Klinefelter syndrome, Turner syndrome, Smith-Magenis syndrome, Angelman syndrome, 21-Hydroxylase-Deficient Congenital Adrenal Hyperplasia, 2q37 Microdeletion syndrome, 3q29 Recurrent Deletion, Achondroplasia, ADNP-Related Intellectual Disability and Autism Spectrum Disorder and melanocortin 4 receptor (MC4R) deficiency comprising administering to a subject in need thereof an effective amount of a PDE10A inhibitor selected from the group consisting of 1-[2-fluoro-4-(1H-pyrazol-1-yl)phenyl]-5-methoxy-3-(1-phenyl-1H-pyrazol-5-yl)-pyridazin-4(1H)-one, 1-(4-(3-(4-(1H-Benzo[d]imidazole-2-carbonyl)phenoxy)pyrazin-2-yl)piperidin-1-yl)ethanone, 2-[4-(1-Methyl-4-pyridin-4-yl-1H-pyrazol-3-yl)-phenoxymethyl]-quinoline, and 6-chloro-N-((2,4-dimethylthiazol-5-yl)methyl)-5-methyl-2-(3-(quinolin-2-yl)propoxy)pyrimidin-4-amine, or a pharmaceutically acceptable salt thereof.

2. The method of treating a developmental syndrome according to claim 1 wherein the PDE10A inhibitor is administered in an amount of 0.01 mg to 1500 mg.

3. The method of treating developmental syndrome according to claim 1, wherein the method provides improvement in at least one symptom selected from the group consisting of hypotonia, difficulty in sucking, difficulty in feeding, poor muscle tone, growth hormone deficiency, low levels of sex hormones, a constant feeling of hunger, excessive appetite (hyperphagia), weight gain, obesity, short stature, poor motor skills, underdeveloped sex organs, intellectual disability, learning disability, delayed speech development, delayed language development, infertility, cognitive rigidity, cognitive impairment, emotional lability, obsessive-compulsive behavior, autistic symptomology, psychotic episodes, bipolar disorder with psychosis, excessive daytime sleepiness, scoliosis, osteopenia/osteoporosis, decreased gastrointestinal motility, sleep disturbances, and reduced pain sensitivity.

4. The method of treating a developmental syndrome according to claim 1, wherein the PDE10A inhibitor is administered via a route selected from the group consisting of oral, buccal, sublingual, rectal, topical, intranasal, and parenteral.

5. The method of treating a developmental syndrome according to claim 1, wherein the subject is administered 1 mg to 500 mg of a PDE10A inhibitor or a pharmaceutically acceptable salt thereof.

6. The method of treating a developmental syndrome according to claim 1, wherein the subject is administered 10 mg to 250 mg of a PDE10A inhibitor or a pharmaceutically acceptable salt thereof.

7. The method of treating a developmental syndrome according to claim 1, wherein the total amount of the PDE10A inhibitor or a pharmaceutically acceptable salt thereof administered to the subject in a twenty-four hour period is between 1 mg and 1500 mg.

8. The method of treating a developmental syndrome according to claim 1, wherein the PDE10A inhibitor or a pharmaceutically acceptable salt thereof is administered from one to four times a day.

* * * * *